(12) United States Patent
Korol et al.

(10) Patent No.: US 6,312,713 B1
(45) Date of Patent: Nov. 6, 2001

(54) POLYMER MATRICES FOR STORAGE AND SUSTAINED RELEASE OF DRUGS AND CHEMICALS

(76) Inventors: Bernard Korol, 1014 Bel Air Dr., Highland Beach, FL (US) 33487; Paul Nathan, 4000 Beechwood, Cincinnati, OH (US) 45229

(*) Notice: Subject to any disclaimer, the term of this patent is extended or adjusted under 35 U.S.C. 154(b) by 0 days.

(21) Appl. No.: 09/096,739

(22) Filed: Jun. 12, 1998

(51) Int. Cl.[7] .............................. A61F 13/00; A61L 15/00; A61L 15/16
(52) U.S. Cl. .......................... 424/443; 424/445; 424/446; 424/447; 424/449
(58) Field of Search .................................... 424/443, 445, 424/446, 447, 449

(56) References Cited

U.S. PATENT DOCUMENTS 4,857,334 * 8/1989 Korol et al. .......................... 424/445
5,741,551 * 4/1998 Guire et al. ........................ 427/407.1

* cited by examiner

Primary Examiner—Thurman K. Page
Assistant Examiner—S. Tran
(74) Attorney, Agent, or Firm—Pennie & Edmonds LLP

(57) ABSTRACT

Improved polymeric devices are disclosed which slowly and gradually release drugs or other chemicals, for use as wound dressings that gradually release antibiotics, analgesics, or other useful drugs directly onto the surfaces of wounds. These polymers also provide other sustained-release devices, such as capsules that will gradually release a drug the entire time they remain in the digestive system, until the inert polymer is excreted in feces. These devices are created by reacting: (1) a hydrophilic polymer such as poly(2-hydroxy-ethyl-methacrylate); (2) a solvent such as polyethylene glycol; (3) a plasticizing agent that promotes hydrogen bonding, such as dimethylsulfoxide in a quantity which is substantially reduced compared to prior formulations; and (4) the drug or chemical that is to be slowly released by the final device. The quantity of DMSO has been reduced from about 5%, in previously-known polymer systems, to about 0.1% in these improved devices. This reduction in DMSO content, combined with certain other improvements, doubles the shelf life from 1 year to 2 years, while also eliminating the need to refrigerate these devices until use. The improved polymers also have reduced odors, and reduced discoloration during storage. The new methods and recipes also allow the use of "curing ovens" to accelerate the curing of a liquid slurry into a solidified device. This allows faster, simpler, and more reliable and consistent manufacturing of commercial-scale quantities of these devices.

13 Claims, 1 Drawing Sheet

POLYMER MATRICES FOR STORAGE AND SUSTAINED RELEASE OF DRUGS AND CHEMICALS

BACKGROUND OF THE INVENTION

This invention relates to a polymer matrix system capable of holding and retaining various drugs and chemical agents, and designed to slowly release the drugs or other chemicals over a period of time such as several days. Such polymers are especially useful for preparing relatively thin-layer wound dressings which can release antibiotics or other useful drugs over a period of several days, to help promote rapid and proper healing of wounds.

Numerous types of wound dressings have been disclosed in the prior art for placement over an area of wounded or injured skin, including but not limited to wounds caused by burns. The most closely relevant such dressing is disclosed in U.S. Pat. No. 4,563,184 (Korol, 1986). This wound dressing has a synthetic polymer matrix layer which can incorporate any of various types of antibiotics or other chemical compounds, in a manner which allows the antibiotic to be slowly and gradually released onto the wound surface over a period of several days.

As used herein, terms such as sustained release, extended release, gradual release, prolonged release, or timed release all refer interchangeably to a relatively slow and gradual release of a chemical (such as an antibiotic or other wound-treating drug) from a polymer matrix as disclosed herein, in a manner which causes the chemical to be released at sustained rates over at least about 24 hours. In actual practice, the polymer matrices disclosed herein gradually release antibiotic drugs in a sustained manner over about 4 days or more, when shaped into relatively thin layers that are suitable for use as wound dressings. As discussed below, this level of sustained release is more than enough for the vast majority of intended uses, in treating wounds. Longer release times can be achieved, if desired, by methods such as making the layers thicker, or increasing the concentration of the drug(s).

The polymer matrix is created by mixing a suitable polymer, such as poly(2-hydroxy ethyl methacrylate), which is referred to herein by the acronym PHEMA, with a suitable solvent such as polyethylene glycol with a molecular weight of 400, and a hydrogen-bonding plasticizing agent, such as dimethylsulfoxide (DMSO) or diethylformamide, and allowing them to chemically react under suitable conditions. These three ingredients (i.e., the polymer, the solvent, and the plasticizer) are discussed in more detail below. They can be mixed and then spread as a viscous slurry onto any of several types of substrates, such as a sheet of impermeable plastic or porous fabric, to create a pre-formed bandage. The components of the slurry will then undergo a reaction causing a "curing" of the slurry into a solidified yet flexible and pliable layer, as disclosed in U.S. Pat. No. 4,563,184.

This form of cured polymer matrix system was given the designation "DIMAC", using "di" (pronounced with a long I) from the dimethylsulfoxide component, and "mac" from the methacrylate component.

One clinical application of this new polymer matrix drug storage and delivery system uses the antimicrobial agent silver sulfadiazine, the most often used treatment to prevent infections in 2nd and 3rd degree burns. Although the DIMAC polymer system offered substantial promise as an advancement in the art of wound dressings that can slowly release antibiotics, the technology disclosed in that 1986 patent was never commercialized, due to various factors, including several important shortcomings and limitations in the products which resulted from the methods and recipes that were disclosed in the 1986 patent.

In particular, the preformed sheets of the polymer matrix, when formed by the processes described in U.S. Pat. No. 4,563,184 and used with silver sulfadiazine as the drug which was contained in and slowly released by the matrix, exhibited the following shortcomings: (i) they had to be refrigerated during storage; this was explicitly set forth as a binding requirement, in the Food and Drug Administration (FDA) approval which allowed commercial sale and public use of the product; (ii) even when refrigerated they had a shelf life of only 12 months; and, (iii) they emitted a rather unpleasant garlic-like odor, when a dressing was removed from its storage pouch.

In addition, the processing steps needed to properly manufacture the slurry into a fully cured and solidified final product required long periods of time. These lengthy and tedious manufacturing requirements caused serious drawbacks, including: (i) efforts to develop large-scale manufacturing techniques for making commercial quantities of pre-cured sheets were hindered; and, (ii) the final products made by the manufacturing-scale methods that were eventually settled upon were relatively sensitive and vulnerable to process upsets, leading to worthless and wasted products that did not meet the quality control specifications.

For these and other reasons, the initial version of the DIMAC polymer system, which was licensed at one time to a major health care corporation, was never commercialized.

The Inventor of U.S. Pat. No. 4,563,184 (who is also the same applicant herein) has now created substantially improved methods and recipes for creating DIMAC polymer matrix systems, which can be used as wound dressings that will slowly and gradually release antibiotics onto a wound surface over a period of days.

Accordingly, one object of this invention is to disclose methods and recipes which can eliminate the need to refrigerate the resulting wound dressings during storage.

Another object of this invention is to disclose methods and recipes which can double the shelf life of the polymer matrix systems, from one year (for the old formulations) to at least two years, even though refrigeration is no longer required during storage, as it was for products using the old formulations.

Another object of this invention is to disclose methods and recipes which can eliminate or minimize unpleasant odors from the wound dressings.

Another object of this invention is to disclose methods and recipes which can eliminate or minimize yellowing or other unpleasant discoloration which results from aging of the wound dressings created by such methods.

Another object of this invention is to disclose methods and recipes which allow the use of "curing ovens" to cure the liquid slurry into solid resin form, thereby allowing much faster and greatly simplified manufacturing techniques to be used to make the wound dressings.

All of these objects have been accomplished, as will become apparent through the following summary and descriptions of the preferred embodiments. These accomplishments, especially when combined together within a single article of manufacture, provide a number of major advantages and improvements in the polymer systems disclosed herein, and allow various highly advantageous manufacturing techniques, thereby rendering this product well-suited for commercialization and widespread use among burn victims and other patients.

SUMMARY OF THE INVENTION

Improved synthetic polymer matrices are disclosed which can slowly and gradually release drugs or other chemicals. These polymer matrices are well-suited for use in preparing relatively thin-layered dressings for surface wounds, having any desired size, which will gradually release antibiotics, pain-killing drugs, drugs which can stimulate the growth of new skin, or other useful compounds, directly onto the surfaces of wounds. These improved polymers can also be used to create other devices which can release drugs over a sustained period of time, such as rectal suppositories, and oral-ingestible devices that will gradually release a drug the entire time they remain in the digestive system, until they are excreted in the feces.

These improved polymer matrices are created by mixing and chemically reacting: (1) a hydrophilic polymer, such as poly(2-hydroxy-ethyl-methacrylate); (2) a solvent such as polyethylene glycol; (3) a plasticizing agent that promotes hydrogen bonding with organic compounds, such as dimethylsulfoxide (DMSO), in a quantity which is substantially reduced compared to prior formulations; and (4) the drug or other agent that is to be included in the final polymerized device for slow release when the device is used medically. The quantity of DMSO has been greatly reduced, from about 5% in previously-known polymer systems, to about 0.1% in the improved polymer systems disclosed herein. This reduction in DMSO content, and certain other improvements, provide important advantages including: (i) doubling of the shelf life, from 1 year in the prior art, to 2 years for the improved polymers; (ii) elimination of the need to refrigerate these polymer matrices until they are used; (iii) reduction of unpleasant odors from the resulting polymers; and (iv) reduction of yellowing and other undesired discoloration of the polymer matrices during storage. In addition, the methods and recipes disclosed herein allow the use of "curing ovens", which can use elevated temperatures in combination with treatment such as high-frequency electromagnetic radiation (comparable to microwave cooking) to accelerate curing of a liquid slurry into a solid polymer matrix. This allows faster, simpler, more consistently reliable manufacturing techniques to be used for making these polymers. These advantages are especially important for manufacturing the large quantities that are necessary for commercialization and public use.

DESCRIPTION OF THE PREFERRED EMBODIMENTS

Figure 1:
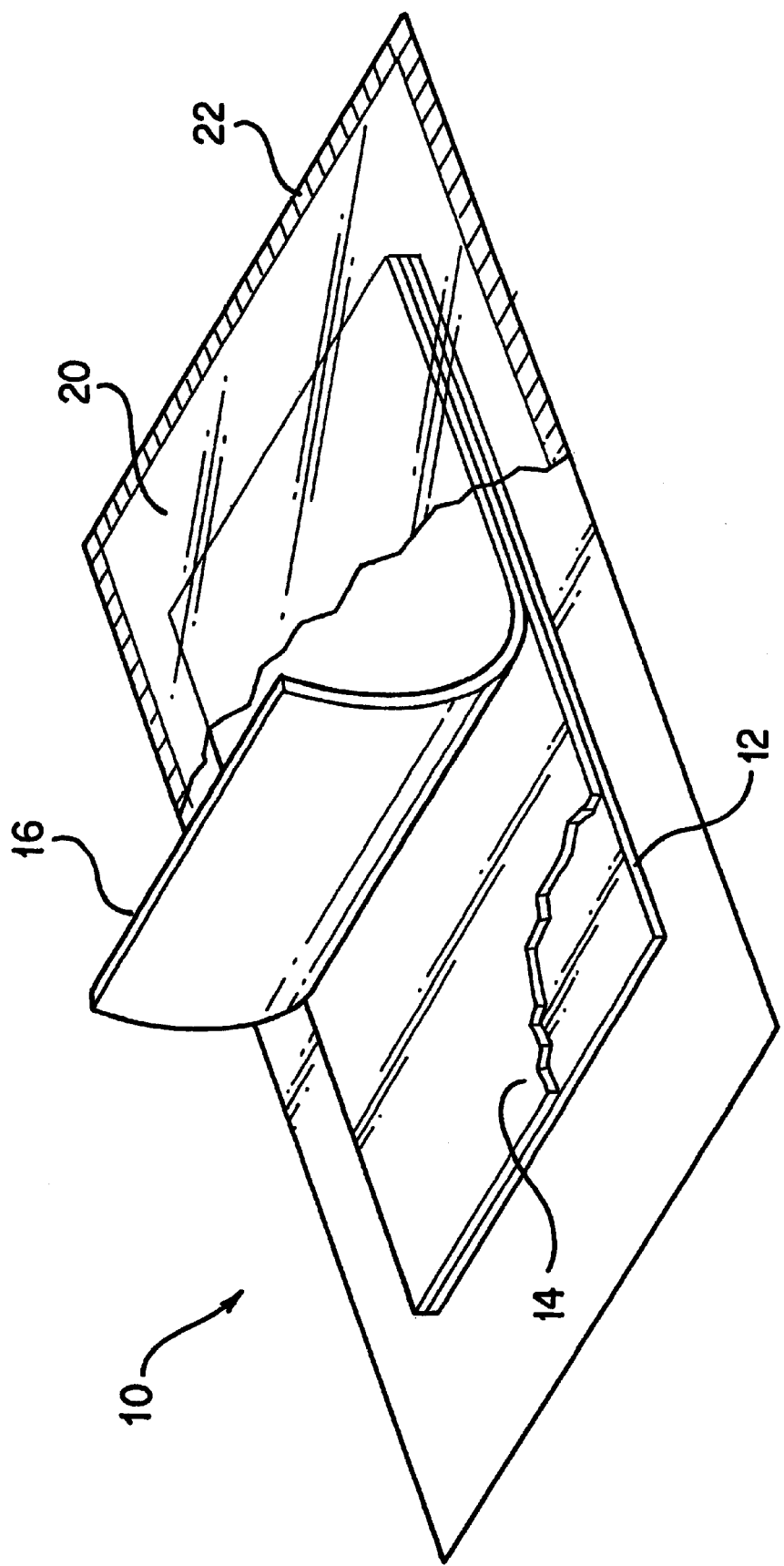
FIG. 1 is a simplified depiction of a wound dressing showing the polymeric matrix embedded in a bidirectionally-elastic nylon fabric, with a removable backing layer, contained in a sealed package.

As summarized above, this invention discloses improved methods and recipes for creating synthetic polymer matrix systems. These polymer matrix systems will gradually release a drug over a sustained period of time, when placed in contact with a wound surface or other moist surface. In general, moisture that is released by the wound surface (or other biological surface or surrounding) will permeate into the polymer, which is hydrophilic. Due to exchange diffusion reactions, the gradual influx of moisture will help promote the sustained release of the drug(s) from the polymer.

In general, the improved DIMAC polymers disclosed herein are relatively inert biologically. They do not gradually dissolve while in use, they are indigestible, and they do not have any noteworthy biological activity. Instead, they effectively provide a containment, storage, and delivery system, comparable in some respects to a porous and permeable sponge that can hold and gradually release a liquid. The DIMAC polymer will not react chemically with the vast majority of drugs, or with other chemical compounds that are useful as topical wound-treating or skin-treating agents or for other medical purposes. In addition, unless steps are taken during manufacturing to introduce a charged compound into the matrix, these polymer matrices have little or no electrical charge, so they will not impede the release of drugs that are electrically charged (such as various salts, which release charged ions).

This combination of traits makes the DIMAC polymer matrices disclosed herein ideally suited for use as thin-layer protective dressings, for burn wounds and other skin wounds. As discussed in more detail below, it also renders them well suited for various other medical uses involving the sustained release of drugs over a period of several days.

The improved DIMAC polymers disclosed herein contain substantially lower levels of DMSO (or an alternate suitable plasticizing agent which promotes hydrogen bonding in the polymer, as discussed below, such as diethylformamide) than previously known DIMAC polymers. In prior U.S. Pat. No. 4,563,184, the lowest DMSO concentrations that were tested and reported in any DIMAC polymers were 2.84% by weight (see Tables 1 and 2, in columns 8 and 9). These concentrations of less than 3% did not provide good results in those early tests, and the preferred concentrations reported in subsequent versions of the DIMAC compounds were greater than 4%, and were typically 5%, as set forth in the various tables contained in U.S. Pat. No. 4,563,184.

By contrast, preferred DMSO concentrations in the improved DIMAC polymers disclosed herein are less than 2%. Polymers containing less than 1% are especially preferred, since they are believed to allow the creation of fully cured polymers that can be stored for at least a year without requiring refrigeration.

The Examples disclose polymers containing only 0.1% DMSO, by weight. This is an especially preferred concentration, since it is sufficiently low to provide fully-cured polymers which can be stored for two years without requiring refrigeration, and which nevertheless (i) provide sustained release of an incorporated drug for at least 24 hours, and (ii) allow for rapid and convenient manufacturing of commercial quantities, with good quality control.

These polymer matrices were initially developed for use as wound dressings, which comprise relatively thin, flexible layers that can slowly release antibiotics or other useful drugs, after placement on a wound surface. However, the recent improvements disclosed herein also allow these improved polymers to be manufactured and used in various other embodiments, as discussed below.

For convenience, these polymer matrix systems are generally referred to herein as "DIMAC" polymers. This name can be modified by adding a prefix to it, to form a similar word which indicates the type of drug that is embedded in the matrix, during storage, and slowly released during use. For example, one variant of DIMAC which contains silver sulfadiazine (which is widely used as an anti-microbial agent, in treating burn wounds) is referred to herein as SILDIMAC™, a registered trademark which is licensed to Cypros Pharmaceutical Corporation, of Carlsbad, Calif., which has licensed the rights to the invention disclosed herein.

Another embodiment of the DIMAC polymer system contains a combination of three different topical antibiotics (neomycin, polymyxin B, and bacitracin), which have been approved, in ointment form, by the U.S. Food & Drug Administration (FDA) for over-the-counter sale and topical use. If these three topical antibiotics are incorporated into a DIMAC polymer system as disclosed herein, the resulting product is referred to by the name MEDIMAC™, which is also a trademark licensed to Cypros Pharmaceutical Corporation.

Other types of drugs and chemicals (such as pain-killing drugs, anti-inflammatory drugs, drugs that accelerate skin growth and wound closure, etc.) also can be contained in (and slowly released by) the polymer matrices disclosed herein, as discussed in more detail, below.

Any of these useful drugs or other chemicals can be readily incorporated into a DIMAC polymer matrix system as disclosed herein, resulting in a drug storage and delivery system which can slowly and gradually release the desired drug(s) directly onto a wound surface that is covered by a wound dressing that is made of the DIMAC polymer. Depending on various parameters, such as the thickness of the polymer matrix layer and the concentration(s) of the incorporated agent(s), the drugs or other chemicals will be released out of the DIMAC polymer matrix system, in a gradual and sustained manner, over a span of about 1 to about 6 days.

It is possible to provide DIMAC matrix systems that will gradually release drugs over even longer periods of time. Although there is not believed to be a great need or demand for wound dressings with that trait (since nearly all physicians would prefer to inspect a wound every few days, and will replace the old bandage with a new bandage during each inspection), such modified polymers with longer sustained-release periods may be suitable for various other medical uses.

One of the most important improvements disclosed herein is a major reduction in the amount of plasticizing reagent (such as dimethylsulfoxide, or DMSO) that is used to prepare the various types of DIMAC polymer matrix systems disclosed herein. In the prior art, as described in Korol's U.S. Pat. No. 4,563,184 (issued in 1986), the preferred formulations contained 5% DMSO by weight. In the improved formulations disclosed herein, the DMSO concentration has been reduced to only 1/50 of that level, to 0.1% by weight.

This major reduction in DMSO content, in combination with various other processing improvements disclosed in the Examples, was found to provide several major and unexpected benefits. Most importantly, it greatly improved the shelf life of the resulting polymer matrix systems that contained silver sulfadiazine. The previous SILDIMAC matrices had an approved shelf life of roughly a year, but had to be refrigerated during storage (refrigeration was a binding requirement, issued by the U.S. Food and Drug Administration as part of its approval of the product).

By contrast, the new and improved polymer matrix system has an FDA-approved shelf life which has been doubled to 2 years; and, even more importantly, that 2-year shelf life can be achieved and has been approved by the FDA without requiring refrigeration.

This major reduction in DMSO content was developed in a way that did not increase the processing time, and which in fact allows shorter overall processing times to be used. This was unexpected, since the prior art clearly and directly teaches in the opposite direction. In specific, U.S. Pat. No. 4,563,184 states, just beneath Table 1 (in column 8): "It was observed that as the amount of DMSO was INCREASED, the set-up time of the resulting wound dressing DECREASED" (emphasis added). A similar statement appears directly below Table 2, which describes in situ curing on the forearm of the experimenter.

In other words, under the prior art, as more DMSO was added, the set-up time grew shorter, as set forth in the time periods listed in Tables 1 and 2 of U.S. Pat. No. 4,563,184. However, that apparent obstacle has been overcome, by careful and diligent improvement of various interrelated and interdependent steps in the manufacturing process, as disclosed in the Examples.

In addition, the reduction in DMSO concentration, coupled with certain other modifications, now allows the use of electromagnetic radiation to facilitate "in-line" curing of the liquid slurry into a semi-solid polymer matrix during the manufacturing process. This treatment, which is comparable to microwave cooking but at a frequency that is usually in the range of several megahertz, can be carried out using commercial-scale equipment sold by companies such as Thermex-Thermatron (Bay Shore, N.Y.).

After the various liquid components are mixed together, they undergo two distinct stages as they set and cure. The first stage is generally referred to as "setting". During this stage, the exposed surface of the slurry develops a skin-like membrane, which no longer has a wet or "tacky" feel. When it reaches this stage, if it is touched by a fingertip or other object, the slurry will not cling in a sticky manner to the object that touches it, so long as the object which touches the surface doesn't poke through the surface "skin" layer.

During the initial setting stage, any treatments that are used to accelerate the setting process must be used with great caution and careful control, since they pose a risk of causing surface irregularities. However, after a "skin" has formed over the surface, when the slurry has set but has not yet fully cured, the risk of surface defects drops substantially, and higher curing temperatures coupled with electromagnetic radiation using fairly high power levels can be used to accelerate the curing of the polymer into a fully solidified but flexible layer.

The treatment parameters that will be preferred for setting and curing a particular type, size, or shape of a DIMAC polymer matrix as disclosed herein will be interrelated with each other. For example, processing times will be shorter for thinner layers of polymer, and when higher temperatures and higher power levels of RF radiation are used to accelerate the curing step. Similarly, if a high degree of cross-linking is desired for a particular device, to create a polymer matrix that will gradually release a drug having a low molecular weight which would permeate too rapidly out of a matrix having lower levels of cross-linking, somewhat different concentrations of the starting reagents would be used, and processing times are likely to be longer, to give the cross-linking reactions more time to occur.

Accordingly, preferred combinations of time, temperature, and RF power for setting and curing a wound dressing (or other device, as disclosed below) made of an improved polymer matrix as disclosed herein can be determined, for any desired thickness or shape, using no more than routine experimentation. To create a sheet of fully cured SILDIMAC polymer matrix with a final thickness that makes it suitable for use as a transparent, flexible wound dressing), suitable processing times are likely to be in the range of about 2 to about 6 hours, for improved DIMAC polymers containing 0.1% DMSO. By comparison, setting and curing times for similar sheets prepared according to the prior art, with 5% DMSO concentration, required about 20 to about 30 hours.

Preferred thicknesses for thin-layer wound dressings are generally in the range of about 0.2 to about 0.5 millimeter (about 0.01 to about 0.02 inch), depending on what type of drug is incorporated into the dressing, and how many days the dressing is expected to be used. In general, SILDIMAC dressings designed for use on burn wounds tend to be designed for longer periods of continuous use, such as up to about 4 days, to give the recovering surface longer periods to grow new skin cells without disruption; accordingly, these dressings will tend to be relatively thick. Dressings which release other types of antibiotics (such as the MEDIMAC-dressings with the triple antibiotic combination as disclosed herein) tend to be thinner, and typically are designed for release of the antibiotics over about 2 days.

FIG. 1 is a simplified depiction of a pre-packaged wound dressing 10 as disclosed herein, shown with the sealed package 20 in cutaway view and with the wound dressing 10 peeled back to illustrate its layers. The bottom layer 12 is made of a porous fabric which preferably can be stretched in an elastic manner in both directions, to give the wound dressing 10 structural support. A layer 14 of the polymeric matrix disclosed herein is coated onto, and partially embedded in, fabric layer 12. To minimize diffusion of the drug out of the polymeric device during storage, the wound dressing is also provided with a removable backing layer 16, made of material such as polyethylene film. The entire device, cut into a convenient rectangular size, is contained inside a sealed watertight package 20, made of a suitable waterproof material such as clear plastic or metallized film, which preferably can allow sterilization of the wound dressing 10 by means such as sterilizing radiation, permeation of a sterliizing gas out of the packaging through one or both layers, etc. The package 20 can be sealed in any suitable manner, such as a heat crimp 22 around the entire periphery.

It should be noted that a curing step accelerated by electromagnetic radiation was also evaluated under the prior art; however, it had to be rejected, since it would have caused substantial discoloration of the old DIMAC formulations which contained 5% DMSO. Accordingly the reduction of DMSO concentration to 0.1% has enabled, for the first time, the use of electromagnetic radiation processing, which can greatly speed up and facilitate commercial-scale manufacturing of these polymer matrix devices containing useful drugs or other chemicals.

It should also be noted that the experts who work at the U.S. Food and Drug Administration, who review drug-delivery devices and compositions of this nature, refused to approve the improved low-concentration DMSO formulations, without requiring extensive testing (by the applicant) of the new formulations with low DMSO concentrations. Regardless of the functional similarities between wound dressing layers created by these new methods, and the wound dressing layers containing the exact same antibiotic compounds by created by the old methods, the experts at the FDA required four years worth of exhaustive and detailed testing, to ensure that the performance of the new and improved products was comparable to the performance of the older products, and that the proposed 2-year shelf life of the improved wound dressings was valid and reliable. This position, taken by independent and impartial reviewers who specialize in this field of medical technology, required the applicant to spend hundreds of thousands of dollars, and literally years of effort and attention, to complete the exhaustive studies that were required by the FDA for the new formulations, even after the old formulations had already been approved. These burdensome requirements, imposed by the FDA's experts, clearly negate and overcome any assumption or inference that the new formulations and manufacturing methods were merely obvious, in view of the old formulations.

THE GRANULAR POLYMERIC COMPONENT

The granular polymeric starting reagent should be a hydrophilic polymer, which will draw water molecules into it and swell up into a flexible, pliable, hydrated form when contacted and saturated with water. As noted above, this hydrophilic trait of the polymer will promote the sustained release of drugs from the polymeric matrix of a wound dressing or other such device, when the polymeric device is in use, contacting a moist surface. The hydrophilic polymeric matrices disclosed herein are manufactured in a manner that is devoid of water; therefore, moisture that is gradually released by a wound surface will be drawn into the hydrophilic device, when the device has been removed from its watertight storage package and placed in contact with a wound surface. This activity (i.e., drawing water into the polymeric matrix) helps displace the drug(s) contained in the device, through a diffusion exchange mechanism, thereby promoting gradual and sustained release of the drug(s) onto the wound surface.

Various types of hydroxylated polymers derived from acrylate are well suited for this purpose, since they are hydrophilic and will swell into soft, pliable, transparent form when contacted by water. These types of polymers are used in soft contact lenses, and for various other biological and medical uses.

Acrylate (the ionized form of acrylic acid) is a building block used in a variety of plastics. Its chemical structure is $H_2C=CH-COOH$. The double bond in this monomeric building block gets opened up and converted into a single bond when the monomer is reacted with itself to form a polymer. When this happens, the pendant carboxyl moiety (—COOH) and anything else that has been attached or substituted to that moiety becomes a side chain that sticks out from the main backbone of the polymer. Since nearly any desired type of molecular group can be substituted at the carboxyl location, while the acrylic acid molecule is still in monomeric form, acrylic acid derivatives are highly adaptable as building blocks for plastics.

"Methacrylate" has a methyl group ($-CH_3$) attached to the #2 carbon atom (i.e., the carbon atom nearest the center of the acrylic acid molecule). "Ethyl-methacrylate" has the same methyl group on the #2 carbon atom, and also has an ethyl group attached at the carboxyl location, through an ester linkage, to form the structure $-COOCH_2CH_3$. When an ethyl-methacrylate monomer is converted into a polymer, that $-COOCH_2CH_3$ structure is converted into pendant side chains, attached to the polymeric backbone which is formed by opening up the double bond.

These acrylate monomers are shown below.

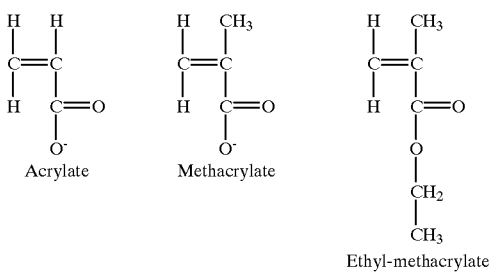

Ethyl-methacrylate

In order to make an acrylate plastic which is hydrophilic (i.e., attractive to water) and which will swell into a soft, flexible, pliable form when saturated with water, a hydroxy (—OH) group can be attached to the side-chain ethyl portion of the ethyl-methacrylate monomer. When this approach is taken, the two carbon atoms that were donated by the ethyl group are numbered as the #1 and #2 carbon atoms, with the #1 carbon attached to the ester linkage, and the #2 carbon out at the far end of the group. This numbering system ignores the numbering system used for the carbon atoms that will form the main polymeric backbone; accordingly, these numbers indicate how the pendant side chains are structured, after the monomer has been polymerized.

Accordingly, the polymer called PHEMA, which is made by polymerizing 2-hydroxy-ethyl-methacrylate, will have a backbone that contains nothing but carbon atoms. On every other carbon atom, a methyl group (—CH$_3$) will be attached, pointing in one direction, while a side chain comprising a 2-hydroxy-ethyl group coupled to a carbonyl group via an ester linkage (giving a total of —COOCH$_2$CH$_2$OH) will also be attached to that same carbon, pointing in another direction. This polymer, known as PHEMA, can be shown as follows:

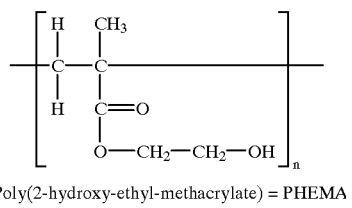

Poly(2-hydroxy-ethyl-methacrylate) = PHEMA

By controlling the polymerization reaction, using various methods known to synthetic chemists, this PHEMA polymer can be made in a range of average molecular weights. In the absence of a solvent, when cooled to room temperature, these polymers typically are sold in granular form, which can be milled into a powdered form if desired. A granular form of PHEMA, purchased from a commercial supplier, was used as the starting reagent herein.

To make slow-release drug delivery devices as disclosed herein, the preferred average molecular weight for the polymeric PHEMA reagent is believed to be in the range of about 500,000 daltons to about 1.5 million daltons. Polymers with molecular weights lower than preferred tend to have inadequate strengths, and are more subject to tearing, while polymers having molecular weights that are too high tend to take too long to set up and cure into cohesive sheets or other devices.

As will be recognized by those skilled in the art of polymer chemistry, other types of hydrophilic polymers that swell into a soft, flexible form when saturated with water can also be used to create devices that have physical properties comparable to devices prepared from PHEMA, using the methods disclosed herein. In many cases, such alternative polymers have molecular structures that are closely related to the structure of PHEMA. As examples, the methyl group in ethyl-methacrylate can be replaced by other lower alkyl groups, such as an ethyl group; the hydroxyl group on the #2 carbon atom of the ethyl group can be placed at a different location on the ethyl group, or the hydroxy-ethyl group can be replaced by a hydroxy-propyl group, or by a 2,3-dihydroxy-propyl group for a higher level of hydrophilicity. U.S. Pat. No. 4,563,184 lists and claims a number of other alternative polymers which can be used if desired. Any of these polymers can be synthesized, using methods that are well-known to synthetic chemists, and they can be evaluated for use as described herein, using no more than routine experimentation.

It should also be noted that polymers prepared from acrylamide monomers, rather than monomers derived from acrylic acid (acrylate), can be used, as disclosed in U.S. Pat. No. 4,563,184. Acrylamide is identical to acrylic acid, with the exception that a primary amine group (—NH$_2$) is substituted for the —OH group in the carboxylic acid portion of acrylic acid. Like a carboxyl group, one of the hydrogen atoms on the pendant primary amine group of an acrylamide monomer can be substituted with almost any desired substituent, to provide a monomer (and a final polymerized compound) have a desired combination of physico-chemical traits.

Since the final device as disclosed herein should be relatively inert biologically, and will merely serve as a slow-release delivery system for a drug that is incorporated into the device, the traits that are primarily relevant herein include: (i) an ability to create a thin sheet (or other shaped device, as described elsewhere herein) with sufficient tensile and cohesive strength to retain its structural integrity (which includes resistance to cracking, splitting, or other loss of occlusive protection, to keep out bacteria and viruses) during its intended use on or in a patient; (ii) sufficient flexibility and pliability to allow a thin sheet of the final material to be placed in a conforming manner over a body portion being treated, such as an elbow or knee; (iii) compatibility with an exposed wound surface, such as a third degree burn, which has suffered severe damage to or loss of the dermal layer; (iv) the wound dressing (or other device) must not leach out any compounds that might irritate the wound; however, this constraint does not prohibit the release of any DMSO or polyethylene glycol from the device, since both of those solvent-type compounds are widely used in skin-contacting topical preparations, and in small quantities do not have any adverse effects on wounds or other skin surfaces;

THE PEG AND PLASTICIZER COMPONENTS

The solvent that is used in the reagent mixture must act in concert with the plasticizer, to soften the granular or powdered polymer and cause the polymer to take on a controllable shape. In addition, the solvent must also be miscible with water (i.e., it must be mixable with water, in any proportions), so that it will not block or impede the process whereby moisture that is being drawn into the polymeric device from a wound surface will help to displace and gradually release the drug that is contained in the polymer.

PEG 400 (this refers to polyethylene glycol which has an average molecular weight of 400 daltons) is a preferred solvent with a good combination of characteristics for such use. It is organic and will mix thoroughly with granular or powdered PHEMA (especially in the presence of DMSO). Because it has multiple hydroxyl groups coupled to the organic backbone, it is miscible with water, and can be used to create products that are compatible with aqueous surfaces, such as an exposed third-degree burn wound. Accordingly, PEG 400 appears to be very well-suited for the use disclosed herein, and it has a long history of safe use in topical medical formulations.

If desired, other water-miscible organic solvents can be evaluated for use as disclosed herein, using no more than routine experimentation. Candidates for such use include various alcohols, sugar-alcohols, and other polyhydroxylated organic compounds having molecular weights in ranges that render them useful as solvents during mixing.

It is currently believed and assumed that the solvent chosen for use as disclosed herein should not directly react with the polymer, in a manner that would cause covalent cross-linking of the polymer. It is believed that the reactions disclosed herein between a PHEMA polymer, PEG solvent, and DMSO plasticizer do not lead to substantial formation of covalent cross-linking binds in the final product. Instead, without tying this invention to any specific type or theory of molecular interaction, the cohesive strength of the thin layers disclosed herein is believed to arise from: (i) using a solvent mixture to thoroughly dissolve a polymer having a desired molecular structure and a desired average molecular weight, in a manner that causes the long polymeric backbones and the relatively short side chains to become entwined and entangled with each other while in liquefied or slurry form, and then (ii) removing a sufficient quantity of the solvent to leave the residual mixture (including the entwined polymer molecules and a substantial residual quantity of the solvent molecules) in a flexible and pliable form.

This process is rendered practical, efficient, and able to withstand minor variations in the polymer or PEG solvent, by the use of a plasticizing agent which is believed to have a suitable level of "hydrogen bonding" activity.

In chemical terms, "hydrogen bonding" refers to a type of molecular attraction that is widely used in nature to hold things together in a stable but reversible manner. For example, the two strands of DNA in a double helix are held together by hydrogen bonding; this allow the strands to remain together, in a chromosomal gene, for the life of the cell, but it also allows the two strands to be pulled apart without damaging them, in order to allow the two strands to be temporarily opened up so that one of the strands can be transcribed to form RNA, which subsequently leaves the nucleus of the cell.

Hydrogen bonding relies on the fact that a hydrogen atom, when covalently bonded to a carbon or other atom in a methyl group ($-CH_3$) or similar organic group, has a mildly positive externally-directed local charge. This occurs because the proton which forms the hydrogen nucleus will be positioned on the exposed/external side of an electron pair that forms the covalent bond between the carbon atom and the hydrogen nucleus. Since the positively-charged hydrogen proton is located outside the negatively-charged electron pair, the net result, on the surface of the molecule, is a localized positive charge at that location.

This localized positive charge is attracted to an "unshared electron pair" that is exposed on the surface of an electronegative atom, such as an oxygen, nitrogen, or sulfur atom in a larger molecule. DMSO has a sulfur atom in the center, with a pendant oxygen atom coupled to that sulfur atom (via a double bond), and no hydrogen atoms are bonded to the oxygen atom. Therefore, DMSO has a relatively strong localized negative charge, with two unshared electron pairs exposed on the surface of the oxygen atom. This localized negative charge causes DMSO to be attracted to pendant methyl groups, and to other organic groups with localized positive charges.

Similarly, diethylformamide also promotes hydrogen bonding, due to the presence of a pendant oxygen atom and a nitrogen atom in proximity to each other, in an amide bond arrangement. During some early tests, diethylformamide was substituted for DMSO, and it performed in a comparable and apparently satisfactory manner. DMSO was chosen as the preferred plasticizing agent during subsequent research, due to various factors such as lower cost, greater ease of handling, and a long history of safe use in skin-contacting formulations. Nevertheless, diethylformamide, other lower-alkyl formamide compounds, and other plasticizing compounds (especially those which have a pendant oxygen atom in proximity to another electronegative atom such as sulfur or nitrogen) can also be evaluated for use as described herein, if desired.

In the wound dressings and other devices of this invention, this type of stable-but-reversible hydrogen bonding plays a crucial role in the following processes: (i) pulling and drawing together the PHEMA polymer molecules and the PEG solvent molecules, thereby increasing their ability to mix intimately with each other, and increasing the ability of the PEG solvent to soften and swell the granular PHEMA particles; (ii) reducing the amount of time that is required during a manufacturing operation to cause a mixture of PHEMA, PEG, and DMSO to be fully mixed, and then to set up and cure into a fully-formed sheet or other device with adequate tensile strength; and (iii) creating a final cured sheet that is flexible, pliable, and easy to work with and manipulate, but which also resists drying, cracking, splitting, hardening, and other problems that would reduce its shelf life during storage, and that would reduce or jeopardize its utility when applied to a wound surface.

Because of all these factors, DMSO (and the hydrogen bonding activity it brings to the processes and products disclosed herein) plays a crucial role in this invention. Accordingly, it was not surprising that the prior art (in U.S. Pat. No. 4,563,184) disclosed and taught that the amount of curing and manufacturing time that was required to create thin-layer wound dressings was higher, in devices that contained inadequate levels of DMSO. As noted above, the preferred mixtures disclosed in the prior art contained 5% DMSO.

What was unexpected and surprising are the new discoveries disclosed and claimed herein, as follows: (1) it is entirely feasible to use mixtures containing only 0.1% DMSO, which is only ¹⁄₅₀ of the amount required under the prior art; (2) despite the greatly reduced DMSO concentration, the manufacturing process has actually been speeded up, rather than slowed down, by taking advantage of other aspects of the reagent mixture, which can now be treated using processes such as electromagnetic radiation to accelerate curing; and, (3) the products generated by these new and improves recipes have a shelf life of 2 years, without refrigeration, compared to a shelf life of only 1 year even under refrigeration, for the devices of the prior art.

DRUGS THAT CAN BE INCORPORATED INTO WOUND DRESSINGS AND OTHER DIMAC DEVICES

When the polymer matrices disclosed herein are formed into thin-layer sheets for use as wound dressings, these devices can incorporate, store, and gradually release any of numerous different types of drugs or other chemicals, which are collectively referred to herein as "wound-treating topical agents". Examples of wound-treating topical agents that can be contained and released by these DIMAC polymers include:

(1) anti-microbial compounds that contain silver, such as silver sulfadiazine. This compound is very widely used for treating burn wounds, since it has broad-spectrum anti-microbial activity, and does not pose a severe risk of an undesired allergic or immune response;

(2) other types of antibiotics, such as a combination of three topical antibiotics (neomycin, polymyxin, and bacitracin) that are widely used in ointments that are commonly called "triple antibiotic" or "NEOSPORIN"™ ointments;

(3) hormones, such as hormones that stimulate the growth or division of fibroblasts or other types of skin cells, follicular cells, nerve cells, etc.;

(4) anti-inflammatory compounds, such as hydrocortisone and various salts and derivatives thereof, other similar drugs derived from steroids, and various "non-steroidal anti-inflammatory drugs" (NSAID's, such as ibuprofen and naproxen) which can help reduce pain and/or inflammation;

(5) topical pain-reducing agents (such as benzocaine, lidocaine, etc.) that can reduce pain, itching, and/or other unwanted neuronal activity, by mechanisms such as stimulating inhibitory neuronal receptors that are normally triggered by gamma-amino-butyric acid (GABA) or other neurotransmitters that inhibit, rather than stimulate, nerve cell activation;

(6) drugs which have anti-nausea, anti-convulsant, or other desired effects, such as scopolamine or other agents that can help reduce unwanted neuronal activity by blocking or reducing neuronal stimulation caused by excitatory neurotransmitters such as acetyl-choline, glutamate, or aspartate;

(7) drugs which can reduce cravings, such as cravings for nicotine, alcohol, or other substances that can impair recovery by a seriously injured patient;

(8) zinc compounds that help promote wound healing (see, e.g., M.S. Agren, "Studies on zinc in wound healing," *Acta Dermato-Venereology, Supplement* 154: 1–36 (1990) and U.S. Pat. No. 4,847,083 (Clark 1989)) and which can reduce the risk of viral infection (e.g., Y. J. Gordon et al, "Irreversible inhibition of herpes simplex virus replication in BSC-1 cells by zinc ions," *Antimicrob. Agents Chemother.* 8: 377–380 (1975), and U.S. Pat. No. 5,545,673 (Kelly 1996)); and, (9) drugs that can help modify and control the rate of connective tissue growth and/or blood vessel growth in badly burned or otherwise damaged tissue. In some situations, growth-accelerating drugs are used to accelerate the wound-closure process, even at the risk of increased fibrotic scar tissue, in locations where the scars will not be highly visible, or when a massive burn or chemical wound or similar injury poses a severe threat of death. In other situations, such as facial or hand wounds where cosmetic appearance and skin flexibility are very important, other types of drugs might be used to minimize the creation of fibrotic scar tissue.

Any of the above-listed agents (alone or in combination) can be incorporated into polymer matrices as disclosed herein, in forms which are fabricated and intended for use to cover burn wounds or other types of skin wounds, and for similar types of topical use in which a thin-layered device is placed directly on the surface of the skin at an appropriate location in the body.

It should also be recognized that topical administration of various drugs can be a desired route of administration in various cases, for any of numerous reasons. Topical administration avoids the high acidity of the stomach, as well as the enzymatic and other digestive processes that tend to attack and degrade anything that is ingested orally. Topical administration also avoids the need to have a specific molecular substance extracted from the mass of material passing through the intestines, transferred across the intestinal membranes, and deposited in the circulating blood. In addition, if two drugs undergo undesired cross-reactions, competition for uptake through the intestinal membranes, or similar interference, it may be possible to use transdermal administration to minimize or avoid such cross-reactions or competition, thereby allowing effective simultaneous use of both drugs in ways that cannot be accomplished if both drugs are administered by the same route.

Accordingly, for various drugs that are not well-suited for oral ingestion, and for patients suffering from various medical problems, topical administration may be preferred over other routes. Any such drug which is a candidate for topical administration can be evaluated for use with the improved polymer matrix systems disclosed, using routine experimentation.

To a limited extent, the rate of diffusion of a drug or other chemical out of the improved DIMAC polymers disclosed herein also is a function of the size and molecular weight of the drug or other chemical, since small molecules tend to permeate out of a matrix somewhat more rapidly than large molecules. In general, it is believed that any drug or other compound with a molecular weight of less than about 700 to about 1000 daltons is likely to permeate out of the DIMAC matrices disclosed herein, without any special modification, in a desirably gradual and sustained manner, over a period of several days. Other drugs or chemicals which have larger molecular sizes or weights can also be evaluated for use with the DIMAC polymeric matrices disclosed herein, using no more than routine experimentation. If necessary to accommodate and gradually release any particular drug or other chemical, the polymeric matrices may modified if desired, such as by using a PHEMA polymer with a lower molecular weight as one of the starting reagents.

In addition, as disclosed in the following section, the polymer matrices disclosed herein can also be adapted and used for various other types of medical uses.

EMBODIMENTS AND USES OTHER THAN WOUND DRESSINGS

The improved DIMAC matrices disclosed herein can be used to provide flexible semi-solid devices which can be used in a variety of situations and modes, to slowly and gradually release, over a period of several days, drugs or other chemicals that have been incorporated into the matrices. Examples of such alternate modes of use (other than thin-layer wound dressings) include:

1. a suppository, which can be inserted rectally;
2. a sub-lingual device, such as a wafer that is designed to be placed under the tongue;
3. a lozenge-type device that will not dissolve in the mouth, which can be sucked on for a first period of time to gradually release an initial quantity of drug, and which can be subsequently chewed on and mashed down between the molars, to release additional drug;

4. an orally ingested device, as discussed in more detail below and in Example 4;
5. a device which can be placed in contact with the eyeball, similar to a contact lens, to treat a condition such as glaucoma or an eye infection;
6. skin patch designed to release a hormone (such as estrogen), a cardiovascular drug (such as nitroglycerin), a drug which reduces cravings for nicotine, alcohol, or illicit drugs, or any other suitable drug or chemical that can permeate through the skin;
7. devices which can be emplaced in the nasal cavities. Such devices may be useful in various ways, such as treating a serious sinus infection in an infant or a senile patient who will not reliably take medication in other ways, or for delivering a drug such as calcitonin for the treatment of a condition such as osteoporosis.

An orally-ingested DIMAC device can be taken as a pill, comparable to a tablet or capsule. The improved DIMAC matrices described herein are relatively indigestible; they will not dissolve in the acidic conditions of the stomach, and they are not attacked by the proteolytic and other enzymes that digest food in the intestines. Therefore, if a DIMAC device (comparable to a gelatinous pill which contains an incorporated drug) is swallowed, it will release the drug, in a gradual and sustained manner, over a period of about 8 to about 24 hours (depending on what else the patient has eaten), while the device travels through the intestinal tract. The device will then be excreted in the feces, like an indigestible pellet or fibrous material. If desired, a pill of this nature can be covered by an enteric coating, made of a compound such as keratin that does not dissolve in the stomach, to protect the drug from the stomach acidity, comparable to the "gel-cap" gelatin-coated capsules that are widely used for various drugs.

Other devices which are made of DIMAC polymer matrices, or which incorporated a DIMAC polymer matrix as one component in the device, can also be implanted under the skin, either by surgical means or by injection through a large-bore needle under local anesthesia. However, unlike various other known polymers which gradually dissolve and disappear in contact with bodily fluids, the DIMAC polymer will not dissolve and disappear, once it is inside the body. This is a design constraint which limits, but does not eliminate, the use of DIMAC polymers in devices that are implanted surgically or subcutaneously.

EXAMPLES

Example 1
Fabrication of DIMAC in Thin Sheet for Wound Dressing

The following reagents were mixed together by mechanical stirring in the following proportions, by weight: polyethylene glycol with an average molecular weight 400, 61%; poly(2-hydroxy ethyl methacrylate, in a granular/powdered form, 39%; and dimethylsulfoxide: 0.1%. A batch containing 120 kg total weight was mixed at a mildly chilled temperature (about 10° C.) until proper consistency and viscosity was achieved. During this process, the granular PHEMA swelled up and became a soft, gelatinous-type mass, as the PEG 400 solvent and DMSO molecules permeated into the polymeric lattices of the PHEMA.

The resulting mixture was spread evenly across a waterproof polyethylene film, by means of a device using a flat blade over a roll coater, to form a wet sheet having a relatively even thickness of 0.021 inch (about 0.53 mm). To give the polymer structural support, a woven mesh made of a nylon "Lycra" material which is elastic in both directions (purchased from Tweave, Inc. of Norton, Massachusetts) was layered on top of the chemical mixture. The three-layer combination was rolled up and cured at room temperature for a minimum of 18 hours.

When subsequently cut into 4 inch by 6 inch rectangles, each dressing contained about 7 grams of the polymeric matrix. When ready for use as a wound dressing, the polyethylene film could be cleanly peeled away from the chemical layer. The nylon mesh and chemical mixture, which adhere to each other, would be applied to the wound and kept in place by wrapping a layer of gauze or other suitable bandaging material around the limb or other body area, to secure the dressing in place over the wound.

Example 2
Incorporation of AgSD into SILDIMAC Dressing

A "SILDIMAC" dressing was prepared by using the same steps as set forth in Example 1, with the addition of silver sulfadiazine (AgSD) to the chemical slurry at a final concentration of 1% by weight. After set-up and curing, the wound dressing was tested in vitro for anti-microbial activity against two types of bacteria that pose a major threat of infecting burn wounds, *Pseudomonas aeruginosa* and *Staphylococcus aureus*. The SILDIMAC dressings were shown to release AgSD in effective anti-microbial concentrations for at least 4 days.

Example 3
Triple Antibiotic in MEDIMAC Wound Dressing

A "MEDIMAC" dressing containing neomycin sulfate (3.5 mg per gram of chemical mixture), polymyxin B sulfate (10,000 units/g), and bacitracin zinc (500 units/g) was prepared by using the same steps as set forth in Example 1, with the additional incorporation of the three antibiotic agents listed above into the reagents used to create the chemical mixture. After set-up and curing, the wound dressing was tested in vitro for anti-microbial activity against a panel of various microbes that pose serious threats of topical infection. The MEDIMAC bandages were shown to have effective anti-microbial activity for at least 2 days.

Example 4
Ingestible Pellets for Sustained Enteric Release

A chemical slurry containing PHEMA, PEG 400, and DIMAC was prepared as described in Example 1. Either of two drugs (diltiazem, which is a cardiac medicine, or urapidil, an anti-hypertensive drug used for bladder control) were incorporated into these slurries.

Aliquots of the drug-containing slurries were placed inside capsules made of an enteric coating material that dissolves in the digestive tract. The polymeric slurry cured into solidified form inside the capsules.

The capsules, which were properly sized for oral ingestion by dogs, were fed to dogs. Subsequent blood tests showed that both of the drugs (separately) were released into the circulating blood of the dogs in a gradual and sustained manner, over a period of about 12 to 15 hours. These relatively broad plateaus were a substantial improvement compared to orally-ingested conventional capsules, which caused relatively sharp peaks followed by relatively rapid drop-offs in drug concentrations in the blood.

Thus, there has been shown and described a new and useful method for creating relatively inert polymeric matrices that can gradually release a variety of useful drugs and chemicals. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

What is claimed is:

1. A method of preparing a sustained-release drug delivery device comprising the steps of:
   (a) combining and chilling a hydrophilic polymer, a water-miscible solvent, a hydrogen-bonding plasticizing agent, and a drug to form a fluidized mixture, wherein the hydrogen-bonding plasticizing agent is at a concentration of 0.1% to 1.0% by weight;
   (b) shaping the fluidized mixture into a medically useful shape; and
   (c) allowing the fluidized mixture to set and cure, thereby forming a solidified polymeric matrix having a medically useful shape.

2. A method of preparing a sustained-release drug delivery device comprising the steps of:
   (a) combining and chilling a hydrophilic polymer, a water-miscible solvent, a hydrogen-bonding plasticizing agent, and a drug to form a fluidized mixture, wherein the hydrogen-bonding plasticizing agent is at a concentration of about 1.0% by weight;
   (b) shaping the fluidized mixture into a medically useful shape; and
   (c) allowing the fluidized mixture to set and cure, thereby forming a solidified polymeric matrix having a medically useful shape.

3. A method of preparing a sustained-release drug delivery device comprising the steps of:
   (a) combining and chilling a hydrophilic polymer, a water-miscible solvent, a hydrogen-bonding plasticizing agent, and a drug to form a fluidized mixture, wherein the hydrogen-bonding plasticizing agent is at a concentration of about 0.5% by weight;
   (b) shaping the fluidized mixture into a medically useful shape; and
   (c) allowing the fluidized mixture to set and cure, thereby forming a solidified polymeric matrix having a medically useful shape.

4. A method of preparing a sustained-release drug delivery device comprising the steps of:
   (a) combining and chilling a hydrophilic polymer, a water-miscible solvent, a hydrogen-bonding plasticizing agent, and a drug to form a fluidized mixture, wherein the hydrogen-bonding plasticizing agent is at a concentration of about 0.1% by weight;
   (b) shaping the fluidized mixture into a medically useful shape; and
   (c) allowing the fluidized mixture to set and cure, thereby forming a solidified polymeric matrix having a medically useful shape.

5. The method of claims 1, 2, 3 or 4 further comprising, after step (c), step (d) packaging the solidified polymeric matrix in a watertight package.

6. The method of claims 1, 2, 3, or 4, wherein the hydrophilic polymer comprises a hydrophilic derivative of acrylic acid or acrylamide.

7. The method of claims 6, wherein the hydrophilic polymer comprises a polymerized acrylate or acrylamide compound having hydroxyl groups bonded to pendant side chains that are bonded to a polymeric backbone.

8. The method of claim 7, wherein the hydrophilic polymer comprises poly (2-hydroxy-ethyl-methacrylate).

9. The method of claims 1, 2, 3 or 4, wherein the plasticizing agent comprises dimethylsulfoxide.

10. The method of claim 1, 2, 3 or 4, wherein the fluidized mixture is treated by means of electromagnetic radiation, to accelerate curing of the fluidized mixture into the solidified form.

11. The method of claim 1, 2, 3 or 4, wherein the delivery device is a flexible wound dressing.

12. The method of claims 1, 2, 3 or 4, wherein the delivery device is placed on a fabric layer.

13. The method of claims 1, 2, 3 or 4, wherein the delivery device is placed on a removable backing layer.

* * * * *